United States Patent [19]

Merchant et al.

[11] Patent Number: 6,136,364
[45] Date of Patent: Oct. 24, 2000

[54] MICROCAPSULE FLAVOR DELIVERY SYSTEM

[75] Inventors: Zohar M. Merchant; Vikki J. Nicholson, both of Chicago, Ill.

[73] Assignee: Kraft Foods, Inc., Northfield, Ill.

[21] Appl. No.: 08/302,596

[22] Filed: Sep. 8, 1994

[51] Int. Cl.[7] ..................................................... A23D 7/04
[52] U.S. Cl. ........................ 426/602; 426/601; 426/651
[58] Field of Search .................................. 426/601, 602, 426/650, 651; 264/4.1; 428/402.2

[56] References Cited

U.S. PATENT DOCUMENTS

| | | | |
|---|---|---|---|
| 4,515,769 | 5/1985 | Merritt | 426/651 |
| 4,590,086 | 5/1986 | Takahashi | 426/602 |
| 4,626,443 | 12/1986 | Takahashi | 426/602 |
| 4,626,444 | 12/1986 | Takahashi | 426/602 |
| 4,632,840 | 12/1986 | Takahashi | 426/602 |
| 4,714,566 | 12/1987 | Takahashi | 426/602 |
| 4,908,154 | 3/1990 | Cook et al. | 252/314 |
| 4,931,210 | 6/1990 | Takahashi | 426/602 |
| 4,933,192 | 6/1990 | Darling et al. | 426/98 |
| 4,944,956 | 7/1990 | Brun et al. | 426/592 |
| 4,971,721 | 11/1990 | Takahashi et al. | 252/314 |
| 4,985,173 | 1/1991 | Takahashi | 426/602 |
| 4,988,456 | 1/1991 | Takahashi | 426/602 |
| 5,045,337 | 9/1991 | El-Nokaly et al. | 426/602 |
| 5,139,803 | 8/1992 | Haynes et al. | 426/330 |
| 5,322,704 | 6/1994 | Gaonka | 426/601 |
| 5,332,595 | 7/1994 | Gaonkar | 426/650 |

FOREIGN PATENT DOCUMENTS

| | | | |
|---|---|---|---|
| 0040874 | 12/1981 | European Pat. Off. | 426/602 |
| 0076549 | 4/1983 | European Pat. Off. | 426/602 |
| 58-165732 | 9/1983 | Japan | 426/602 |
| 58-165737 | 9/1983 | Japan | 426/602 |
| 59-210972 | 11/1984 | Japan | 426/602 |

OTHER PUBLICATIONS

Magee, Jr., et al., "Microencapsulation of Cheese Ripening Systems: Formation of Microcapsules", J. Dairy Sci. 64:600–610, 1981.

*Primary Examiner*—Carolyn Paden
*Attorney, Agent, or Firm*—Fitch, Even, Tabin & Flannery

[57] ABSTRACT

The present invention is directed to a method for producing a microcapsule flavor delivery system. In the method, a mixture of a flavoring material selected from the group consisting of an oil soluble flavor dissolved in an oil and an o/w emulsion flavor and a protein solution is provided. The mixture is subjected to low shear mixing to provide an o/w water pre-emulsion. The pre-emulsion is subjected to high shear mixing or sonication to provide an o/w emulsion having a coating of protein around the internal oil droplets. The o/w emulsion is mixed with a liquified hard fat which is solid at room temperature. The mixture of hard fat and o/w emulsion is atomized onto a planar surface or into a fluid to provide microcapsules which are an o/w/o multiple emulsion having a flavoring material in the internal oil phase or o/w emulsion.

11 Claims, No Drawings

MICROCAPSULE FLAVOR DELIVERY SYSTEM

FIELD OF THE INVENTION

The present invention relates generally to a method for producing a microcapsule flavor delivery system which is an oil-in-water-in-oil emulsion. More particularly, the present invention is directed to a microcapsule having a stabilized flavor material in the core of the microcapsule.

BACKGROUND OF THE INVENTION

Emulsions, in general, are heterogeneous systems of one immiscible liquid dispersed in another in the form of droplets which usually have a diameter greater than 1 micron. The two liquids are chemically unreactive and form systems characterized by a low thermodynamic stability. Simple emulsions are classified according to the nature of their continuous and dispersed phase. It is the custom to set forth the droplet (dispersed) phase first followed by the continuous phase separated by a / mark, i.e., either water (droplets)-in-oil (continuous) (w/o) or oil-in-water (o/w) emulsions. Multiple emulsions are characterized by listing the primary emulsion set first which is dispersed in a continuous phase. For example, in a water-in-oil-in-water (w/o/w) multiple emulsion, a w/o primary emulsion is dispersed in a water continuous phase. An emulsifier is present to stabilize the emulsion and a variety of ionic and non-ionic surfactants are available for this purpose. Lipophilic (oil-soluble, low HLB) surfactants are used to stabilize w/o emulsions, whereas hydrophilic (water-soluble, high HLB) surfactants are used to stabilize oil/water systems.

Multiple emulsions are more complex systems as the drops of the dispersed phase themselves contain even smaller dispersed droplets which normally consist of a liquid which is miscible, and in most cases, is identical with the continuous phase. They are, therefore, emulsions of emulsions. For each type of multiple emulsion, the internal and external phases are alike and an intermediate phase separates the two like phases. The intermediate phase is immiscible with the two like phases.

Multiple emulsions are usually prepared by a two-stage procedure, Matsumoto, et al., *J. Colloid Interference Sci.*, 57-353–361 (1976). The first stage involves the preparation of a primary emulsion, which, in the preparation of a o/w/o emulsion, is an o/w emulsion. In the second step, the primary emulsion is further emulsified in oil containing a lipophilic emulsifier to form the multiple emulsion. The primary emulsion may be prepared in any suitable manner; for example, with a laboratory mixer, by ultrasonication, etc. A hydrophilic emulsifier is used to promote the formation of an o/w emulsion. This emulsion is then poured into a solution or a dispersion of a lipophilic emulsifier in oil. The lipophilic emulsifier is used to promote w/o emulsification in which the "water" phase is the o/w emulsion.

The second emulsification step is critical and sometimes extremely difficult to effect as excess mixing can fracture the drops of the primary emulsion, resulting in a simple w/o emulsion. The internal oil droplets are lost and mixed with the external oil phase as the water drops are torn apart. For this reason, high shear mixers and sonication are unsuitable methods for preparation of the second emulsion. A low-shear mixer may be employed or the mixture may be shaken by hand. However, no matter what emulsification method is used for the second step, some of the internal oil phase is usually lost to the external oil phase.

With respect to food technology, considerable research effort has been expended on developing reduced fat food products which have low oil content, particularly aqueous based products which have low or substantially no fat content. Significant advances have been made in reducing fat and oil content of various food products through the use of, for example, water-in-oil emulsions or water-in-oil-in-water emulsions, wherein water occupies volume which otherwise would have been occupied with oil, thereby commensurately reducing the amount of oil in an oil-containing food product. For example, Takahashi, et al., U.S. Pat. Nos. 4,632,840, 4,626,443 and 4,626,444 disclose reduced fat salad dressings having a w/o/w emulsion base. Such salad dressings nevertheless still have about 30% oil by weight. Further fat reductions have been obtained using, as fat mimetics, novel carbohydrate-protein complexes such as those disclosed in U.S. Pat. No. 5,104,674 or microreticulated microcrystalline cellulose as disclosed in co-owned U.S. Pat. No. 5,011,701 filed Aug. 18, 1989. Such carbohydrate-protein complexes or microreticulated microcrystalline cellulose are particularly useful in providing no-fat food products such as viscous and pourable salad dressings and the like having fat-like organoleptic characteristics.

While elimination or substantial reduction of oil content is attainable, such low-fat or no-fat products characteristically lack (or lose during storage) the desirable flavor possessed by their high-fat counterparts. Stabilization of lipid-soluble flavors in low- or no-fat, aqueous based food products has not received much attention. Heretofore, aqueous soluble flavors have merely been added along with other aqueous soluble ingredients to produce low- or no-fat food products; with respect to reintroducing fat-soluble flavors to reduced-fat products. PCT International Application No. WO90/00354 to Singer discloses adding to low-fat and no-fat foods, fat globules containing concentrated fat soluble flavoring to simulate the organoleptic effect of fat-rich food products. In each of these cases, the flavors are in contact with the aqueous based food vehicle environment (either directly or at the interface between the fat globules and the aqueous base of the food vehicle) and thereby may be adversely affected. Flavor perception in low- or no-fat food products containing soluble flavors simply mixed into the aqueous-based food vehicle, e.g., viscous or pourable salad dressings or the like, rapidly deteriorates; presumably due to interaction of flavors with the aqueous base, giving such products a short shelf life. It would therefore be desirable to provide food products (especially no-fat products) which have aqueous or oil soluble flavor components stably maintained so as to protect the flavors from volatilization, oxidation and other undesirable events, during extended storage, while at the same time providing for ready release of such flavors, with good organoleptic characteristics, when such low/no-fat food products are eaten.

The o/w/o microcapsule flavor delivery system of the invention is simple and straight forward. It results in encapsulating the oil soluble flavor as well as oil and water soluble flavors which may be in a paste or water continuous emulsion form. The encapsulated o/w/o microcapsules are stable in aqueous products especially low/no-fat products, including shelf stable, refrigerated and frozen products. There is no detrimental effect on mouthfeel, as the microcapsules release the flavor in the mouth or when heated in the oven. The flavor delivery system of the invention may also be used to incorporate fat-soluble vitamins or other oil or oil-in-water emulsion soluble components and can be used to protect oils which may be susceptible to oxidation.

SUMMARY OF THE INVENTION

The present invention is directed to a method for producing a microcapsule flavor delivery system. In the method, a mixture of a flavoring material selected from the group consisting of an oil soluble flavor dissolved in an oil and an o/w emulsion flavor and a protein solution is provided. The mixture is subjected to low shear mixing to provide an o/w pre-emulsion. The pre-emulsion is subjected to high shear mixing or sonication to provide an o/w emulsion having a coating of protein around the internal oil droplets. The o/w emulsion is mixed with a liquified hard fat which is solid at room temperature. The mixture of hard fat and o/w emulsion is atomized onto a planar surface or solution to provide microcapsules which are an o/w/o multiple emulsion having a flavoring material in the internal oil phase or o/w emulsion.

DETAILED DESCRIPTION OF THE INVENTION

Oil soluble and o/w emulsion soluble flavors are coated with a protein coat followed by forming an o/w/o emulsion which is stabilized by forming microcapsules. The process of the invention involves providing a flavor dissolved in an oil or an o/w emulsion flavor and adding it to a protein solution to form an o/w pre-emulsion. The pre-emulsion is then subjected to either high shear mixing or high intensity sonication to generate a protein coat surrounding the oil droplet. The o/w emulsion containing protein coated oil droplets is then added to a liquified fat which is a solid fat at room temperature in the presence of an emulsifier to form an o/w/o emulsion. This emulsion is then subjected to atomization to form stable o/w/o microcapsules. The flavors that can be encapsulated in this fashion include dairy (water continuous paste), pizza (water continuous paste) and an oil soluble model flavor.

The protein source can be egg white proteins, serum proteins, milk proteins and other food proteins containing thiol groups. The internal oil can be any oil compatible with the above system. Emulsifiers may be used if necessary and can be either ionic or nonionic. The external fat/oil can be butterfat, hydrogenated oils including soybean oil, partially hydrogenated cottonseed oil, rapeseed oil, other hard fats or combinations thereof.

The oil in the o/w pre-emulsion can be any suitable vegetable oil. Generally, the oil is selected from the group consisting of soybean oil, corn oil, cottonseed oil, coconut oil, palm kernel oil, safflower oil, neobee oil, canola oil, peanut oil and olive oil. The oil is present in the o/w pre-emulsion at a level of from about 30% to about 90%. All percentages used herein are by weight unless otherwise indicated.

The hard fat may be any animal or vegetable fat which is solid at room temperature. Generally, the hard fat is selected from butterfat, lard and fully or partially hydrogenated vegetable oils. Preferred vegetable oils are cottonseed oil, soybean oil, corn oil, coconut oil, palm kernel oil and peanut oil. The hard fat is present in the mixture of the hard fat and o/w pre-emulsion at a level of from about 30% to about 70% and the o/w pre-emulsion is present at a level of from about 70% to about 30%.

The flavoring material is present in the oil of the o/w pre-emulsion at a level of from about >0% to about 90%. The oil with the flavoring material present is used in the pre-emulsion at a level of from about 30% to about 90%.

The protein is present in the protein solution used to prepare the o/w pre-emulsion at a level of from about 1% to about 11%. The protein solution is present in the mixture of a soluble flavor dissolved in an oil or an o/w emulsion flavor at a level of from about 10% to about 70%.

The o/w/o emulsion containing the protein coated flavoring oil is atomized to provide the microcapsules. One suitable method for forming the microcapsule of the o/w/o emulsion is to spray the emulsion onto a spinning planar surface or into a fluid, such as an aqueous solution. The plate is preferably cooled to a temperature in the range of from about 0° F. to about 72° F. prior to spraying the emulsion. The method of the invention is particularly suitable for applying a pizza flavor to a frozen pizza crust. The frozen pizza crust is placed onto a spinning plate and the o/w/o emulsion is sprayed onto the surface of the pizza crust as it spins to provide an even coating of the emulsion. The microcapsules produced by the method of the present invention have a particle size in the range of from about 20 microns to about 200 microns.

The following examples further illustrate various features of the invention, but are not intended to limit the scope of the invention as set forth in the appended claims.

EXAMPLE 1

Encapsulated Pizza Flavor o/w/o Microcapsules

Liquid egg white solution containing 0.9% sodium chloride was added to an o/w pizza flavor emulsion (1:4 w/w) to provide a pre-emulsion. The pre-emulsion was mixed on a Brinkman Polytron PT3000 using PT-DA 3012/2S generator, Kinematica Ag Switzerland for 30 s at 5000–6000 rpm. The resulting emulsion was sonicated in a Branson Sonifier Cell Disruptor 200 at 40% power (80 Watts for 60 s) to form a stable o/w emulsion with a protein coat.

The protein coated o/w flavor emulsion (24 g) was added under mixing at 5000 to 10,000 rpm (Brinkman Polytron PT3000 using PT-DA 3012/2S generator) to an oil blend (80:20 w/w hydrogenated palm kernel oil and cottonseed flakes maintained at 50° C., 36 g) containing 2.5% phosphorylated monoglyceride (EMPHOS™). The resulting o/w/o emulsion maintained at 50° C. was sprayed onto a 9 inch diameter frozen pizza crust placed on a spinning disc using a hollow cone nozzle (2.0 mm orifice, 70° cone) under 80–120 psi nitrogen pressure. This yielded a layer of 20–27 g o/w/o pizza flavored microcapsules per frozen pizza crust (500 g). The particle size analysis performed on a Horiba LA-500 revealed average size of 100 microns. Typically 2 pizza crusts could be sprayed per 60 g (o/w/o) batch size. The samples were stored frozen in a freezer prior to evaluation.

EXAMPLE 2

Unencapsulated Pizza Flavor w/o Microcapsules

A w/o emulsion was made by adding 24 g water to 36 g of an oil blend (80:20 w/w/ hydrogenated palm kernel oil and cottonseed flakes) containing 2.5% phosphorylated monoglyceride (EMPHOS™) maintained at 50° C. The w/o emulsion was formed by shearing the oil phase at 11,000 rpm with a Brinkman Polytron PT 3000 and slowly adding the aqueous phase. The temperature of the w/o emulsion was maintained at 50–55° C. and w/o microcapsules were formed by spraying the w/o emulsion onto a pizza crust as described in Example 1. An equivalent amount of flavor was applied as described in Example 1.

EXAMPLE 3

Evaluation of Release of Flavor from Frozen Pizza Flavored Crusts

The release profile of the pizza flavor from the o/w/o microcapsules was evaluated by placing the frozen pizza crust containing the o/w/o flavor in a conventional oven set at 450° F. (232° C.). The aroma release was evaluated by monitoring sensorially the aroma profile over a 20 minute time period with a group of 7 people. The release profile of encapsulated pizza flavored o/w/o microcapsules was balanced and different than samples containing either pizza flavor paste spread on the frozen pizza crust alone or unencapsulated pizza flavor paste. Also, the flavor was delayed and persisted for a long time with the encapsulated sample versus appearing early and disappearing fast for the unencapsulated samples.

EXAMPLE 4

Encapsulated Dairy Flavor o/w/o Microcapsules

Dairy Powder 100 (o/w paste dairy flavor, (6.0 g) was added to egg white (3.0 g) and emulsified at low shear (6000 rpm) until homogeneous. The solution was then sonicated to form an o/w emulsion. The o/w emulsion was then mixed with 16.0 g of a higher melting fat (e.g., 20% cottonseed flakes/80% hydrogenated palm-coconut oil) with 2.5% EMPHOS™ at 50° C. where the fat level was 60 to 65%. The temperature was maintained and the mixture sprayed onto a spinning plate with a metal surface at room temperature. The spraying pressure was 80 to 120 psi with a spray rate of 1.8 g/sec using a hollow cone stainless steel nozzle. The sheet of microcapsules that was formed was placed in a conventional oven at 450° F. (232° C.) and aroma release evaluated sensorially. The release profile of the encapsulated sample was delayed and persisted for a longer time than the non-encapsulated sample.

What is claimed is:

1. A method for producing a microcapsule flavor delivery system comprising:
   (a) providing a mixture of a flavoring material selected from the group consisting of an oil soluble flavor dissolved in an oil and an o/w emulsion flavor and a protein solution;
   (b) subjecting said mixture to low shear mixing to provide an o/w pre-emulsion;
   (c) subjecting said pre-emulsion to high shear mixing or sonication to provide an o/w emulsion having a coating of protein around the internal oil droplets;
   (d) mixing the o/w emulsion with a liquified hard fat which is solid at room temperature to provide an o/w/o emulsion; and
   (e) atomizing the o/w/o emulsion onto a planar surface or into a fluid to provide microcapsules having a flavoring material in the internal oil phase, said microcapsules having a particle size of from about 20 microns to about 200 microns.

2. A method in accordance with claim 1 wherein the protein in said protein solution is selected from the group consisting of egg albumin, lactalbumin, lactoglobulin and casein.

3. A method in accordance with claim 1 wherein said oil in which said flavor is dissolved is selected from the group consisting of soybean oil, corn oil, cottonseed oil, coconut oil, palm kernel oil, neobee oil, safflower oil, canola oil, peanut oil and olive oil.

4. A method in accordance with claim 1 wherein said hard fat is selected from butterfat, lard and fully or partly hydrogenated vegetable oils.

5. A method in accordance with claim 1 wherein said hard fat is liquified by heating said hard fat to a temperature in the range of from about 110° F. to about 130° F.

6. A method in accordance with claim 1 wherein microcapsules are produced by spraying the mixture of step (d) onto a spinning plate or into a fluid.

7. A method in accordance with claim 1 wherein said flavor is an oil soluble pizza flavor and said microcapsules are produced by spraying said o/w/o emulsion onto the surface of a pizza crust which is positioned on a spinning plate.

8. A method in accordance with claim 7 wherein said pizza crust is frozen.

9. A method in accordance with claim 1 wherein said protein solution has protein present at a level of from about 1% to about 11%.

10. A method in accordance with claim 1 wherein said flavoring material is present in said o/w pre-emulsion at a level of from about >0% to about 90%.

11. A method in accordance with claim 10 wherein said o/w pre-emulsion is present in said mixture with said hard fat at a level of from about 30% to about 70%.

* * * * *